United States Patent [19]

Harms et al.

[11] Patent Number: 5,207,678
[45] Date of Patent: May 4, 1993

[54] PEDICLE SCREW AND RECEIVER MEMBER THEREFORE

[75] Inventors: Jürgen Harms, Waldbronn Reichenbach; Lutz Biedermann, Schwenninger, both of Fed. Rep. of Germany

[73] Assignee: Prufer, Munich, Fed. Rep. of Germany

[21] Appl. No.: 817,659

[22] Filed: Jan. 7, 1992

[30] Foreign Application Priority Data

Jul. 20, 1989 [DE] Fed. Rep. of Germany ....... 3923996

[51] Int. Cl.$^5$ ............................................. A61B 17/56
[52] U.S. Cl. ............................................. 606/61; 606/72; 606/73
[58] Field of Search ................. 606/72, 73, 75, 61

[56] References Cited

U.S. PATENT DOCUMENTS

| 3,875,936 | 4/1975 | Volz | 606/73 |
| 4,611,580 | 9/1986 | Wu | 606/61 |
| 4,771,767 | 9/1988 | Steffer | 606/61 |
| 4,805,602 | 2/1989 | Puno | 606/61 |
| 4,887,596 | 12/1989 | Sherman | 606/73 |
| 4,913,134 | 4/1990 | Lugue | 606/73 |
| 5,005,562 | 4/1991 | Cotrel | 606/61 |
| 5,042,982 | 8/1991 | Harms | 606/61 |
| 5,067,955 | 11/1991 | Cotrel | 606/61 |
| 5,092,867 | 3/1992 | Harms | 606/61 |

FOREIGN PATENT DOCUMENTS

| 0242708 | 10/1987 | European Pat. Off. |
| 3711013 | 6/1988 | Fed. Rep. of Germany ........ 606/61 |
| WO91/01115 | 2/1991 | PCT Int'l Appl. |

Primary Examiner—Robert A. Hafer
Assistant Examiner—Michael Brown
Attorney, Agent, or Firm—Donald Brown

[57] ABSTRACT

For a pedicle screw a receiver member is provided for hingedly connecting a screw (2) comprising a threaded shaft portion (3) and a spherical-segment-shaped head (4) on the one hand and a rod (16) on the other hand. In order to improve the stocking costs for screws of different shaft lengths and shaft diameters, the receiver member has a receiver chamber (7) therein, the receiver chamber has a bore (8) at one end thereof for passing the threaded shaft portion (3) followed by an inner hollow spherical-segment-shaped portion (9) for supporting the head of the screw (2) to be received, and an aperture (10) on the side opposite to the bore (8) for inserting the screw (2). Further, a compression member (18) is provided which exerts, in assembled state, a force onto the head such that the head is pressed against the hollow spherical-segment-shaped portion (9). The new receiver member provides that only screws with different screw shafts must be stocked and in operation these screws can be then assembled with the uniform receiver members.

7 Claims, 1 Drawing Sheet

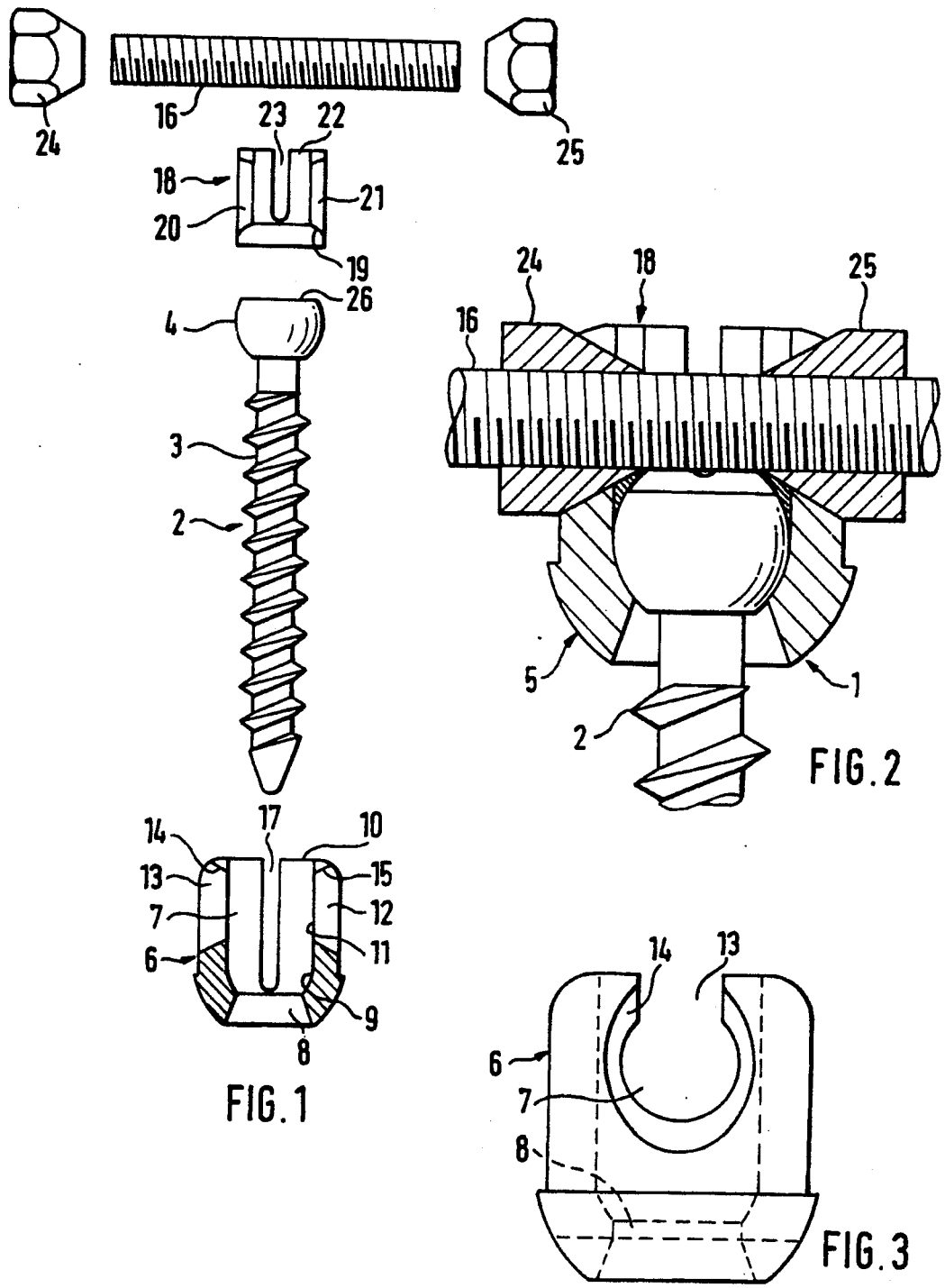

PEDICLE SCREW AND RECEIVER MEMBER THEREFORE

The invention relates to a receiver member for a pedicle screw for a hinged connection of a screw which comprises a threaded shaft portion and a spherical or sphericalsegment-shaped head, with a rod as well as a pedicle screw for stabilisation of spinal column segments.

The DE-AS 26 49 042 discloses a pedicle screw comprising a threaded portion and a receiver member rigidly connected to the head end thereof. A plurality of pairs of such screws are screwed into the vertebra in a respective distance from each other on both sides of the spinal column. The individual receiver members comprise receiver slits. A respective threaded rod is passed through the receiver slits of the right and left, resp., group of screws. By means of locking screws the rod is then located at the respective receiver member. A drawback of this solution consists in the difficulty to rigidly screw the screws into the vertebra and at the same time exactly place the screws in two planes such that the axes of the receiver slits in the superposed or stacked receiver members are aligned such that the threaded rod can be passed through the receiver slits without distorting the screws. Already the attempt to do this requires a lot of time which is a serious drawback for an operation at the spinal column. Further, such an exact alignment can hardly be achieved. As a result considerable sheering forces act upon the threaded rods which may even cause breaking of the rods during later use after the end of the operation.

The EP 0 242 708 A discloses a pedicle screw consisting of the screw proper having a threaded shaft portion and a spherical or spherical-segment-shaped head and of a receiver member hingedly connected thereto. The receiver member comprises two head halves which are retained by means of a ring and which comprise on their facing inner sides portions formed as segments of a hollow sphere which surround the head in assembled state such that the head is retained in the thus formed hollow sphere allowing a pivoting movement around the center of the hollow sphere. This provides a very well operating pedicle screw. However, in an operation screws of different lengths and eventually also different diameters are required. When using this known screw, it is necessary to have the entire screws in the desired sizes on stock. However, the stocking costs for such complete screws are very high because of the required high precision of the two shell halves having the two spherical-segment-shaped portions and of the ring retaining these parts.

It is the object of the invention to provide a possibility for reducing the stocking costs of such screws.

This object is achieved by means of a receiver member according to claim 1.

A pedicle screw formed with such a receiver member is characterized in claim 2.

Further embodiments of the invention are characterized in the subclaims.

The invention achieves that only the screw shafts with various lengths and thicknesses, but uniform heads must be stocked. The stocking costs are considerably reduced thereby.

Further features and objects of the invention will stand out from the description of an embodiment with reference to the drawings. In the drawings FIG. 1 shows an exploded side view of the pedicle screw with receiver member, partly in sectional representation, and FIG. 2 shows a section through the receiver member with the screw being inserted and the rod being connected with the receiver member, in an enlarged representation.

FIG. 3 shows a side view from a direction turned by 90° around the axis of symmetry with respect to the representation of FIG. 1 on an enlarged scale.

The pedicle screw 1 comprises the actual screw 2 having a threaded shaft part 3 and a spherical segment-shaped head 4 formed unitarily therewith, as well as the receiver member 5.

The receiver member 5 comprises a housing 6 for receiving the screw 2. The housing has a receiver chamber 7 therein. In axial direction of the receiver chamber this chamber is defined at one end thereof by a bore 8 having a diameter which is smaller than twice the radius of the spherical-segment-shaped portion of the head 4. A portion 9 in the form of a hollow spherical segment is provided in the interior immediately adjacent to the bore. The radius of this portion is substantially equal to the radius of the spherical segment-shaped portion of the head 4. The hollow spherical-segment-shaped portion 9 changes directly to a hollow cylindrical portion 11 extending to an aperture 10 opposite to the bore 8. The diameter of the portion 11 is slightly larger than twice the radius of the spherical-segment-shaped portion of the head 4 by such an amount that the head 4 can be inserted, when inserting the screw 2 into the receiver member, into the position shown in FIG. 2 in which the head contacts the hollow spherical-segment-shaped portion 9. As in particular shown in FIG. 2 the bore 8 is aligned coaxially to the axis of the cylindrical portion and has, viewed from inside to outside, the form of a cone portion with outwardly flaring or diverging wall. This enables a swinging movement of the inserted screw around the axis of the hollow cylindrical portion within an angular range defined by the diameter of this cone portion.

The housing has two receiving slits 12, 13 provided in a distance from the hollow spherical-segment-shaped portion 9 and mutually offset or displaced by 180°. The receiver slits 12, 13 extend parallel to the axis of the hollow cylindrical portion 11 and open towards the aperture 10. Each receiving slit has a respective recess 14, 15 at the outside in the same manner as the pedicle screw described in the aforementioned EP 0 242 708 A. The width of the receiving slits is selected such that a threaded rod to be received may loosely be passed therethrough. As best shown in FIG. 1, the housing further comprises two slits 17 which are offset around the axis of symmetry of the housing by 90° with respect to the receiving slits 12, 13 and which extend from the aperture 10 about to the inner edge of the receiver chamber 7.

Further, a compression member 18 formed as a cylindrical insert is provided. The outer diameter of the cylinder is substantially equal to the inner diameter of the hollow cylindrical portion 11 and slightly smaller by such a small amount that the compression member can slide within the hollow cylinder. As best shown in FIG. 1, the compression member is preferably formed as a hollow cylinder. The end thereof facing the hollow spherical-segment-shaped portion when inserting the compression member into the housing 6 also has a portion 19 formed as a hollow spherical segment. The radius of curvature thereof substantially equals the radius of curvature of the hollow spherical-segment shaped portion 9 and the radius of the spherical-segment-shaped portion 4.

The compression member 18 further comprises two receiving slits 20, 21 corresponding to the receiving slits 12, 13 for receiving the threaded rod 16. The receiving slits 20, 21 extend parallel to the axis of symmetry of the compression member in a distance from the hollow spherical-segment-shaped portion 19 to the opposite aperture 22 of the compression member. Again, two opposite slits 23 are provided offset around the axis of symmetry by 90° with respect to the receiving slits. The slits 23 start from a position immediately above the hollow spherical-segment-shaped portion 19 and open to the opposite side.

Further, nuts 24, 25 are provided which serve the purpose of connecting the rod 16 with the pedicle screw in the manner shown in FIG. 2

Basically it is possible to form the head 4 in the shape of a sphere on the side thereof facing away from the threaded shaft portion 3. In this case, the receiving slits and the recesses in the housing 6 have to be selected such that the rod 16 lies in a sufficient distance above the head to prevent that the head contacts the rod or the screws holding the rod when pivoting or swivelling the screw. Preferably the end of the head facing away from the threaded shaft portion 3 has a plane surface 26 extending normally to the screw axis. A recess is provided therein for engagement with a screw driver tool for rotating the screw.

Before inserting the pedicle screw the screw 2 having the desired shaft diameter and length is assembled in the position shown in FIG. 2 such that the sphericalsegment-shaped portion of the head rests within the hollow spherical-segment-shaped portion. Then the screw is screwed into the respective vertebra by engaging the recess within the head 4 with the appropriate tool. After this screwing-in (or before, if desired) the compression element is inserted in the manner best shown in FIG. 2 into the hollow cylindrical-shaped portion 11 such that the hollow spherical-segment-shaped portion 19 of the compression member rests on the spherical region of the head 4. The receiving slits of housing 6 and compression member 18 are aligned to be parallel with each other. Thereafter the rod 16 to be connected thereto is inserted into the receiver slits and rigidly connected thereto by tightening the nuts 24 and 25. The base of the receiving slits 20, 21 is offset towards the free end of the slits by such an amount that an additional pushing force acts onto the head 4 in direction towards the hollow spherical-segment-shaped portion when tightening the nuts holding the screw. Owing to the slits 17 and 23 the cylindrical wall of the housing 6 can slightly yield such that the clamping force acting onto the head is increased. By providing the compression member 18 it is achieved that during such compression which is required for sufficient support the head is completely surrounded by a hollow spherical segment region and pressed through the compression member in direction of the hollow sphericalsegment-shaped portion 19 rather than pressed from the intimate contact with the hollow spherical-segment-shaped portion 19 into the interior. Thereby a rigid lock of the adjusted angular position is achieved.

We claim:

1. Device for stabilizing spinal column segments, comprising a pedicle screw (1) having a threaded shaft portion (3) and a spherically-shaped head (4) at the end of said threaded shaft portion, a receiver member (5) flexibly connected to said head (4), said receiver member being provided with two holes for receiving a rod 916), a receiver chamber (7) being provided within said receiver member (5), the receiver chamber (7) having at one end thereof a bore (8) for passing the threaded shaft portion (3) therethrough and an inner hollow spherically-shaped portion (9) for receiving the head (4) of said screw (1), an opening (10) being provided opposite said bore (8) for inserting said screw (1), said device further comprising a compression member (18) for exerting a force onto said head (4) such that said head is pressed against the hollow spherically-shaped portion (9).

2. Device according to claim 1, characterized in that said receiver member (5) comprises in the portion thereof facing away from said bore (8) at least one slit (17) extending up to the open side thereof, said receiver member further comprising two mutually opposite slits (12, 13) for passing said rod (16) and for receiving locking nuts (24, 25), the slits (12, 13) being angularly offset with respect to said slit (17).

3. Device according to claim 1, characterized in that the side of the compression member 918) facing the head (4) comprises a hollow spherically-shaped portion (19) directed towards said head.

4. Device according to claim 1, characterized that the radii of the hollow spherically-shaped portions (9, 19) and of the spherically-shaped head (4) are substantially equal.

5. Device according to claim 1, characterized in that said receiver chamber (7) has a hollow cylindrically-shaped portion (11) opposite to the bore (8) and adjacent to the hollow spherically-shaped portion (9).

6. Device according to claim 1, characterized in that said compression member (18) comprises a cylindrical portion having an outer diameter which is substantially equal to the inner diameter of said hollow cylindrical portion (11).

7. Device according to claim 6, characterized in that said compression member (18) comprises two slits (20, 21) aligned with said receiving slits and having a base which extends away from the edge engaging said head (4) by such a distance that an additional compression force acts onto said head in a direction towards the hollow spherically-shaped portion when said nuts (24, 25) holding the rod are tightened.

* * * * *

UNITED STATES PATENT AND TRADEMARK OFFICE
CERTIFICATE OF CORRECTION

PATENT NO.  : 5,207,678
DATED       : May 4, 1993
INVENTOR(S) : Jurgen Harms and Lutz Biedermann It is certified that error appears in the above-indentified patent and that said Letters Patent is hereby corrected as shown below:

On the title page: Item [73], delete "Prufer, Munich, Fed. Rep. of Germany".

Signed and Sealed this

Eleventh Day of November, 1997

Attest:

BRUCE LEHMAN

Attesting Officer

Commissioner of Patents and Trademarks